United States Patent [19]

Lake et al.

[11] 4,094,919

[45] June 13, 1978

[54] HYDROCARBON CONVERSION PROCESSES AND CATALYSTS

[75] Inventors: Ivan James Samuel Lake; Roy John Sampson, both of Middlesbrough, England

[73] Assignee: Imperial Chemical Industries Limited, London, England

[21] Appl. No.: 671,545

[22] Filed: Mar. 29, 1976

[30] Foreign Application Priority Data

Apr. 10, 1975 United Kingdom ............... 14794/75
Apr. 10, 1975 United Kingdom ............... 14793/75

[51] Int. Cl.² .................................................. C07C 5/24
[52] U.S. Cl. ................................. 260/668 A; 252/450; 260/668 R

[58] Field of Search .................... 260/668 A; 252/450

[56] References Cited

U.S. PATENT DOCUMENTS 3,793,384  2/1974  Chenoweth ..................... 260/668 A
3,860,668  1/1975  January ........................... 260/668 A Primary Examiner—Veronica O'Keefe
Attorney, Agent, or Firm—Cushman, Darby & Cushman

[57] ABSTRACT

Isomerization of alkylbenzene hydrocarbons, for example xylenes, using a silica/alumina catalyst whose alumina content has been reduced by at least 1% of the original alumina content, from an original alumina content in the range 2 to 40% by weight to a content of at least 1% by weight.

16 Claims, No Drawings

HYDROCARBON CONVERSION PROCESSES AND CATALYSTS

This invention relates to hydrocarbon conversion processes and catalysts therefor.

In our U.S. Pat. No. 3,793,384 we have described and claimed a process which comprises isomerising an alkyl aromatic hydrocarbon in the presence of a silica/alumina catalyst of which the alumina content has been lessened by from 1 to 35% of the total alumina originally present, the catalyst comprising before treatment to lessen the alumina content 7 to 40% by weight of alumina and containing after treatment at least 6% of alumina by weight.

In our U.S. Pat. No. 3,793,384 we have also described and claimed amorphous silica/alumina catalysts of which the alumina content has been lessened by from 1 to 35% of the alumina originally present, the catalyst comprising before treatment to lessen the alumina content, 7 to 40% by weight of alumina and containing, after treatment, at least 6% by weight of alumina.

The invention of the aforesaid patent was based on the discovery that the catalytic properties of certain silica/alumina catalysts may be improved by removing from them a specified amount of alumina. It is believed that this effect may be due to removal of alumina which is not chemically combined with silica and which is present as alumina particles from a silica/alumina matrix, and/or to the creation of catalytically favourable sites on the surface of the catalyst by the removal of alumina which is combined with silica from the surface of a silica/alumina structure.

The present invention is a modification to the process of our U.S. Pat. No. 3,793,384 and comprises isomerising an alkyl aromatic hydrocarbon in the presence of a silica/alumina catalyst of which the alumina content has been reduced by at least 1% of the total alumina originally present, the catalyst comprising before treatment to lessen the alumina content 2 to 40% by weight of alumina and containing, after treatment at least 1% of alumina by weight.

Preferably, the alumina content of the catalyst has been lessened by from 1 to 35%, more preferably by from 10 to 30% of the total alumina originally present. Preferably, after treatment, the catalyst contains 2 to 6% by weight of alumina.

The alumina content of the catalyst may be lessened by treatment with acids or complexing agents which remove alumina by forming soluble complexes therewith.

Suitable acids are those of which the anions serve to solubilise the aluminum by forming complex ions. Suitable acids include sulphuric acid, hydrochloric acid, hydrofluoric acid, hydrobromic acid, nitric acid and trihaloacetic acids (for example, trichloracetic acid) and mixtures thereof.

Suitable complexing agents comprise chelating agents, for example polar solutions (preferably aqueous solutions) of ethylene diamine tetra-acetic acid or of acetylacetone.

Many other complexing agents may be used especially in the presence of strong acids.

The above compounds will normally be used as solutions in, for example, water or an alcohol having 1 to 5 carbon atoms, for example, a monohydroxy alkane. Suitable solvents may have in their pure state a dielectric constant of at least 5, preferably at least 10, and more preferably at least 20. The dielectric constant of the solvent is the limiting value at low frequencies at atmospheric pressure and a temperature of 25° C.

The optimum duration of contact of the catalyst with a solution of a compound capable of dissolving the alumina is readily established by experiment. Typically a period within the range 10 minutes to 3 days will be found to be suitable. The solution may contain 0.001 to 10 moles/litre of the compound, and preferably 0.001 to 6 moles/litre, and more preferably 0.1 to 2.0 moles/litre of the compound. The conditions of the treatment are chosen so as to optimise the performance of the catalyst. Contact of the catalyst with those solutions preferably takes place at a temperature in the range 0° to 200° C and very conveniently 5° to 40° C. Often, ambient temperature may be found to be suitable. If desired the alumina content may be lessened in several stages, for example by repeated treatment with an aqueous solution of an acid.

The alumina content of the catalyst may also be lessened by contacting it with a gaseous material, for example, hydrogen chloride or hydrogen bromide, which forms a volatile product with the alumina. The material is preferably passed through a bed of the catalyst at an elevated temperature.

The alumina content of the catalyst may also be lessened by contacting it with a solvent as aforesaid, especially water, in the presence of a strongly acidic ion exchange resin. An acidic ion exchange resin may also be used together with a solution of an acid.

After treatment the catalyst is preferably washed with water (particularly if a small volume of treatment solution is used) to remove traces of solution and aluminium and other cations which may be present in the extraction fluid. The washing may be carried out batchwise by leaving the catalyst standing in water, for example at 0° to 100° C for preferably 1 to 24 hours, or by passing water through the catalyst bed, for example by treatment in Soxhlet equipment for similar times.

The catalyst before treatment to lessen its alumina content is preferably a synthetic silica/alumina catalyst having a surface area in the range 50 to 700 square metres/gram, and more preferably 70 to 300 square metres/gram. Its mean pore diameter is preferably in the range 10 to 400, and more preferably 40 to 300A. The pore volume of the catalyst before treatment is preferably in the range 0.20 to 1.20 cc/g., more preferably in the range 0.35 to 0.85 cc/g.

The catalyst may, if desired, be contacted with liquid water at a temperature above 100° C. This is preferably carried out before, or, when an aqueous solution is to be used, during the treatment to lessen its alumina content. Suitable methods of treatment are disclosed in our U.S. Pat. No. 3,836,594.

It is preferred to isomerise alkyl benzenes having at most 4 carbon atoms in each alkyl group, especially the xylenes.

According to a preferred form of the invention one or more xylenes containing less than an equilibrium concentration of paraxylene are isomerised to produce a product having a greater concentration of paraxylene. Such xylenes may, for example, be mixtures of metaxylene together with ethyl benzene, ortho- and/or paraxylene.

According to a further form of the invention one or more xylenes containing less than an equilibrium amount of ortho-xylene are isomerised to produce a product having a greater concentration of orthoxylene.

The isomerisation of xylenes is preferably carried out at a temperature in the range 200 to 600° C, and more preferably 300° to 500° C. It is preferably carried out at a pressure of 1 to 5 atmospheres absolute. It is preferred to carry out the isomerisation in the presence of 100 to 10,0000 parts per million of steam by weight based on the xylenes.

It has been found that especially good catalysts are produced by treatment with nitric or hydrochloride acids or with ethylene diamine tetra-acetic acid. Such catalysts generally have high activities and selectivities in catalysing the desired isomerisation reaction rather than undesired disproportionation reactions in the isomerisation of alkyl benzenes and may also be less prone to carbonisation which necessitates regeneration by burning off carbonaceous deposits.

In a further preferred form of the present invention, the isomerisation process is effected in the presence of a cyclic hydrocarbon which is present in a concentration of 1 to 20% by weight of the feedstock and is selected from octahydroanthracenes, tetralin, decalin, cyclohexane, cyclo-octane, cyclohexylcyclohexane and the alkyl substituted derivatives of these compounds, the catalyst being free from any hydrogenating component. The isomerisation is suitably carried out in the absence of hydrogen. By a "hydrogenating component" is meant a component which would hydrogenate the alkyl benzene to the corresponding naphthene under the conditions of the reaction if hydrogen were present.

Suitable cyclic hydrocarbons include the octahydroanthracenes, tetralin, decalin, cyclohexane, cyclooctane, cyclohexyl, cyclohexane, and their alkyl, especially $C_1$ to $C_4$ alkyl, substituted derivatives, for example methyl cyclohexane and the di, tri and tetra-methyl cyclohexanes, ethyl cyclohexane, ethylmethyl- and diethyl-cyclohexanes.

The cyclic hydrocarbon is present in a concentration of 1 to 20%, preferably 1½ to 12% by weight, of the feedstock. The use of cyclic hydrocarbons in xylenes isomerisation is disclosed in our U.S. Pat. No. 3,860,668 the disclosure of which is herein incorporated by way of reference.

The isomerisation may be carried out in the presence of water vapour in a concentration of, for example 100 to 10,000, and preferably 1000 to 5000 parts per million by weight of the feedstock.

The present invention also comprises an amorphous silica/alumina catalyst of which the alumina content has been lessened by at least 1% of the total alumina originally present, the catalyst comprising before treatment to lessen the alumina content, 2 to 40% by weight of alumina and containing, after treatment, at least 1% by weight of alumina.

Preferably, the alumina content of the catalyst has been lessened by from 1 to 35%, more preferably by from 10 to 30% of the total alumina originally present. Preferably, after treatment, the catalyst contains 2 to 6% by weight of alumina.

Catalysts according to this invention are believed to be useful in hydrocarbon conversion processes which are catalysed by acids, for example, cracking, alkylation, dealkylation and isomerisation. They are also useful as supports for hydroisomerisation catalysts and reforming catalysts.

Embodiments of the present invention are illustrated in the following Examples.

EXAMPLE 1

30g of an amorphous silica alumina catalyst in the form of 4.5 mm. beads and having an alumina content of 5.1% by weight, a surface area of 215 $m^2g^{-1}$, a pore volume of 0.65 $cm^3g^{-1}$ and a mean pore diameter of 121A was soaked in 40 mls. of 3 molar nitric acid for 24 hours. The liquid was then drained off and the mixture topped up with fresh 3 molar nitric acid and left for a further 24 hours. This was repeated twice more with water instead of acid. The catalyst was then dried by passing through it a stream of air at 140° C. It was then placed in an oven at 200° C and left for 5 hours. Analysis of the liquid drainings showed that 21% of the alumina originally present had been removed.

Samples (12 g) of the treated catalyst and the starting material were each tested for performance in the isomerisation of orthoxylene in a glass tubular reactor by the following method.

Each sample was calcined in a stream of air at 550° C for 16 hours. The air was replaced by nitrogen and the catalyst allowed to cool to 450° C. Orthoxylene (99% pure and containing only traces of the other xylenes) was passed over the catalyst at this temperature for 6 hours. The feed rates used and the conversions obtained are given in the following table.

| Catalyst | Treated | Untreated |
|---|---|---|
| Feed rate (ml hr$^{-1}$) | 23.1 | 9.1 |
| % in product of: | | |
| Paraxylene | 7.6 | 7.7 |
| Metaxylene | 34.3 | 34.4 |
| Toluene | 1.6 | 1.8 |
| Trimethyl benzenes | 2.1 | 2.3 |
| Isomerisation | 41.9 | 42.1 |
| Disproportionation | 3.7 | 4.1 |

The treated catalyst was 2.5 times more active and gave significantly less disproportionation conversion at the same isomerisation conversion.

EXAMPLE 2

A silica alumina catalyst in the form of 4.5 mm. beads and having an alumina content of 14.8%, a surface area of 99 $m^2g^{-1}$, a pore volume of 0.33 $cm^3/g^{-1}$ and a mean pore diameter of 149A was treated with 3 molar nitric acid in the same manner as described in Example 1. The amount of alumina removed was 6% of the amount originally present.

The treated material and starting material were tested for performance in orthoxylene isomerisation as described in Example 1. The flow rates used and the product compositions obtained are given in the following Table.

| Catalyst | Treated | Untreated |
|---|---|---|
| Feed rate (ml hr$^{-1}$) | 23.1 | 8.0 |
| % in product of: | | |
| Paraxylene | 7.6 | 7.0 |
| Metaxylene | 34.3 | 33.7 |
| Toluene | 1.7 | 2.2 |
| Trimethyl benzenes | 2.2 | 2.9 |
| Isomerisation | 41.9 | 40.7 |
| Disproportionation | 3.9 | 5.1 |

The treated material was almost three times more active than the untreated material and produced less disproportionation products at a slightly higher isomerisation conversion.

EXAMPLE 3

A silica alumina catalyst in the form of 4.5 mm. beads and having an alumina content of 3.0%, a surface area of 193 m$^2$g$^{-1}$, a pore volume of 0.87 cm$^3$g$^{-1}$ and a mean pore diameter of 180A was treated with 0.5 molar nitric acid by the procedure described in Example 1. The amount of alumina removed was 23% of that originally present.

The treated catalyst and the starting material were each tested for performance in orthoxylene isomerisation as described in Example 1 except that the feed contained 5% cyclohexane. The feed rates used and the product compositions obtained are given in the following table.

| Catalyst | Treated | Untreated |
| --- | --- | --- |
| Feed rate (ml hr$^{-1}$) | 8.0 | 5.4 |
| % in product of: | | |
| Paraxylene | 7.2 | 6.7 |
| Metaxylene | 35.2 | 34.2 |
| Toluene | 1.1 | 1.2 |
| Trimethyl benzenes | 1.4 | 1.5 |
| Isomerisation | 42.4 | 40.9 |
| Disproportionation | 2.5 | 2.7 |

The treated catalyst was about 1.5 times more active than the untreated material and produced less disproportionation products at a greater isomerisation conversion.

EXAMPLE 4

300 g of a silica alumina catalyst in the form of 4.5 mm. beads and having an alumina content of 5%, a surface area of 211 m$^2$g$^{-1}$, a pore volume of 0.64 cm$^3$g$^{-1}$ and a mean pore diameter of 122A were treated with 3 molar nitric acid in the manner described in Example 1. The amount of alumina removed was 21% of that originally present.

The treated material was placed in the stainless steel tubular reactor of a semi-technical unit and calcined at 500° C for 24 hours in a stream of air.

It was then tested for isomerisation performance at 450° C and 1.7 ats. absolute using a mixed xylenes feedstock containing 8.3% paraxylene, 54.1% metaxylene, 24.5% orthoxylene, 8.9% ethyl benzene and 2.0% toluene. To this was added 5% w/w cyclohexane. The weight hourly space velocity was 3.7. In all tests steam was injected with the feed at the level of 0.5% w/w. The paraxylene production and xylenes destroyed with and without cyclohexane in the feed are given in the following table.

| Cyclohexane in feed | 5% w/w | 0% w/w |
| --- | --- | --- |
| Paraxylene production % w/w | 7.7 | 7.2 |
| Xylenes lost % w/w | 1.2 | 2.2 |

In the presence of cyclohexane more paraxylene (as a percentage of the mixed xylenes feedstock) is produced and less xylene is lost to disproportionation products (toluene and trimethyl benzenes).

We claim:

1. A process which comprises isomerising an alkyl aromatic hydrocarbon in the presence of a silica/alumina catalyst of which the alumina content has been reduced by at least 1% of the total alumina originally present, the catalyst comprising before treatment to lessen the alumina content 2 to 40% by weight of alumina and containing, after treatment from 2 to 5% of by weight.

2. A process as claimed in claim 1 in which the catalyst, after treatment to lessen its alumina content, contains 5% by weight of alumina.

3. A process as claimed in claim 1 in which the alumina content of the catalyst has been lessened by treatment with acids or with complexing agents which remove alumina by forming soluble complexes therewith.

4. A process as claimed in claim 1 in which the catalyst before treatment to lessen its alumina content is a synthetic silica/alumina catalyst having a surface are in the range 50 to 700 square metres/gram, a mean pore diameter in the range 10 to 400A, and a pore volume in the range 0.20 to 1.20 cc/g.

5. A process as claimed in claim 1 in which the alkylbenzene is a xylene.

6. A process as claimed in claim 5 in which the isomerisation is carried out at a temperature in the range 200° to 600° C and at a pressure in the range 1 to 5 atmosphere absolute.

7. A process as claimed in claim 5 in which the isomerisation is carried out in the presence of 100 to 10,000 parts per million of steam by weight based on the xylene.

8. A process as claimed in claim 5 in which the isomerisation is effected in the presence of a cyclic hydrocarbon which is present in a concentration of 1 to 20% by weight of the feedstock and is selected from octahydroanthracenes, tetralin, decalin, cyclohexane, cyclo-octane, cyclohexylcyclohexane and the alkyl substituted derivatives of these compounds.

9. An amorphous silica/alumina catalyst of which the alumina content has been lessened by at least 1% of the total alumina originally present, the catalyst comprising before treatment to lessen the alumina content, 2 to 40% by weight of alumina and containing, after treatment, from 2 to 5% by weight of alumina.

10. A catalyst as claimed in claim 9 containing, after treatment to lessen its alumina content, 5% by weight of alumina.

11. A process as claimed in claim 1 in which the catalyst, after treatment to lessen its alumina content, contains 4% by weight of alumina.

12. A process as claimed in claim 1 in which the catalyst, after treatment to lessen its alumina content, contains 3% by weight of alumina.

13. A process as claimed in claim 1 in which the catalyst, after treatment to lessen its alumina content, contains 2% by weight of alumina.

14. A catalyst as claimed in claim 9 containing, after treatment to lessen its alumina content, 4% by weight of alumina.

15. A catalyst as claimed in claim 9 containing, after treatment to lessen its alumina content, 3% by weight of alumina.

16. A catalyst as claimed in claim 9 containing, after treatment to lessen its alumina content, 2% by weight of alumina.

* * * * *